United States Patent [19]

Trinh et al.

[11] 4,391,129
[45] Jul. 5, 1983

[54] SYSTEM FOR MONITORING PHYSICAL CHARACTERISTICS OF FLUIDS

[75] Inventors: Eugene Trinh, Los Angeles; Taylor G. Wang, Glendale, both of Calif.

[73] Assignee: The United States of America as represented by the Administrator of the National Aeronautics and Space Administration, Washington, D.C.

[21] Appl. No.: 246,774

[22] Filed: Mar. 23, 1981

[51] Int. Cl.³ .......................................... G01N 13/02
[52] U.S. Cl. ..................................... 73/64.4; 250/573
[58] Field of Search ....................... 73/64.4, 505, 516; 250/573

[56] References Cited

U.S. PATENT DOCUMENTS 3,864,044 2/1975 Lyshkow ........................ 250/573 X
4,218,921 8/1980 Oran et al. ............................ 73/505
4,260,258 4/1981 Rose et al. ...................... 250/573 X

OTHER PUBLICATIONS

Lucassen, J., *The Shape of an Oil Droplet in an Aqueous Solution with Density Gradient*, in. Journ. of Coll. & Inter. Sci., vol. 70, No. 2, pp. 355-365, Jun. 15, 1979.

Fink, T. R. et al., *Multicell Spinning Drop Interfacial Tensiometer*, in. Rev. Sci. Instr., vol. 49, No. 2, pp. 188-193, Feb. 1978.

Primary Examiner—Charles A. Ruehl
Assistant Examiner—Joseph W. Roskos
Attorney, Agent, or Firm—Paul F. McCaul; John R. Manning; Thomas H. Jones

[57] ABSTRACT

An apparatus and method are described for measuring physical characteristics of a fluid, by placing a drop (16) of the fluid in a bath (14) of a second fluid and passing acoustic waves through the bath. The applied frequency of the acoustic waves is varied, to determine the precise value of a frequency at which the drop undergoes resonant oscillations. The resonant frequency indicates the interfacial tension of the drop (16) in the bath (14), and the interfacial tension can indicate physical properties of the fluid in the drop.

14 Claims, 3 Drawing Figures

SYSTEM FOR MONITORING PHYSICAL CHARACTERISTICS OF FLUIDS

ORIGIN OF THE INVENTION

The invention described herein was made in the performance of work under a NASA contract and is subject to the provisions of Section 305 of the National Aeronautics and Space Act of 1958, Public Law 85 568 (72 Stat. 435; 42 USC 2457).

BACKGROUND OF THE INVENTION

While the measurement of physical properties of a fluid can be determined by a variety of instruments, many of such instruments involve complex and time-consuming processes, and the instruments themselves are expensive. For example, the chemical composition of a fluid can be determined by a mass spectrometer, but the instruments are expensive and require considerable time to make an analysis. The physical characteristics of fluids can be indicated by measuring certain sensitive fluid characteristics. For example, the surface tension of a fluid is highly dependent on its composition, and even small amounts of contaminants or additives can greatly change the surface tension. One technique for measuring interfacial surface tension between the liquids, involves dipping a wire ring into the more dense liquid, pulling up the ring while the denser liquid clings to it, and noting the height at which the clinging liquid breaks away. Another technique is to hold a drop of dense liquid on the tip of a capillary tube, while the tube lies in a lighter liquid, and noting the amount by which the drop of dense liquid sags. However, these techniques require a substantial density difference between the fluids, and neither technique is sensitive and precise enough to enable its widespread practical utilization in determining other characteristics of the fluid.

OBJECTS AND SUMMARY OF THE INVENTION

One object of the present invention is to provide a method and apparatus for determining the interfacial tension of fluids to a high degree of accuracy.

Another object is to provide a method and apparatus for enabling the rapid measurement of physical characteristics of fluids, and the time evolution of such characteristics.

In accordance with one embodiment of the present invention, a method and apparatus are provided which enable the accurate measurement of interfacial tension or other characteristics of fluids. The method includes the introduction of a quantity or drop of a first fluid into a bath containing a second fluid. Acoustic waves are then propagated through the bath while oscillations of the drop are monitored. The frequency of the acoustic waves is varied to determine the precise value of a frequency at which the drop undergoes resonant oscillations. The resonant frequency indicates the surface tension of the drop in the bath with high precision.

The drop can be held in a stable position within the bath, by the application of high frequency waves which produce a standing wave pattern within the bath, that urges the drop toward a node or anitnode of the wave pattern. The oscillations of a drop can be monitored by directing a light beam through the bath, so the beam is interrupted by the drop, and measuring the amount of light in the interrupted beam along a predetermined axis.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
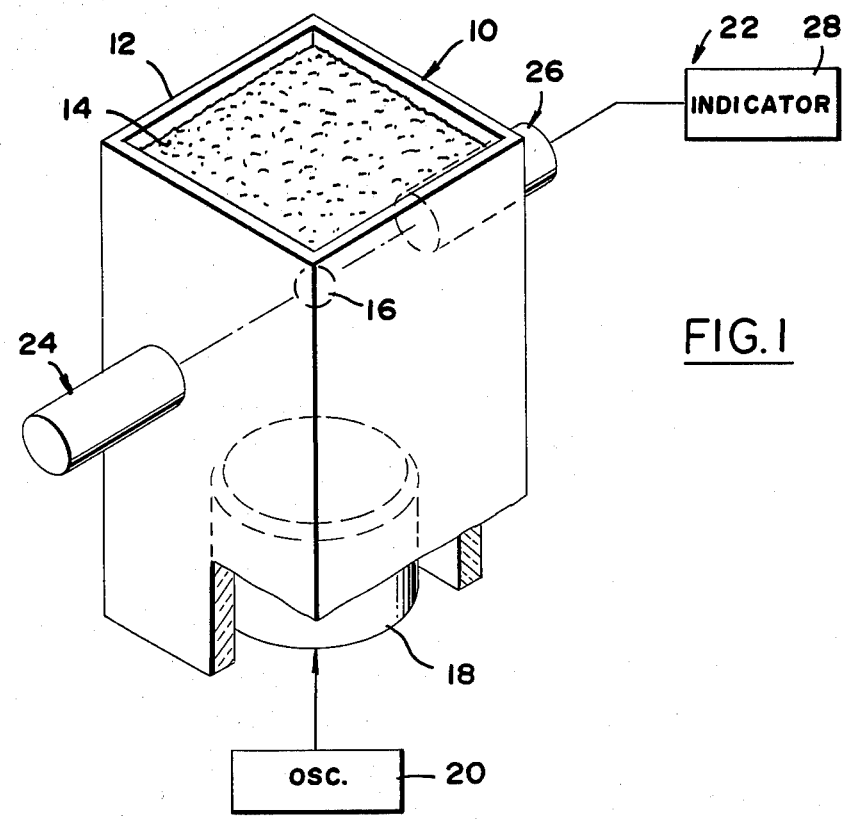
FIG. 1 is a perspective view of an apparatus constructed in accordance with the present invention.

FIG. 1 illustrates an analyzing apparatus 10 which includes a container 12 for holding a host fluid 14 such as water, and with the host fluid being utilized to receive and retain a drop 16 of a second fluid. A transducer 18 is utilized to pass acoustic waves through the fluid bath 14. The acoustic waves include a component of a frequency which produces resonant oscillations of the drop 16. The precise frequency at which the drop oscillates, indicates the interfacial surface tension between the drop 16 and the surrounding fluid bath 14. The transducer 18 is driven by an oscillator apparatus 20, whose frequency output is closely controllable. Oscillations of the drop 16 are monitored by an oscillation sensing device 22 which includes a light source 24 that passes light through the bath area occupied by the drop 16. The light is detected by a detector 26 whose output can be delivered to an indicator 28 to indicate oscillations of the drop.

In order to determine a resonant frequency of oscillation of the drop 16, it is necessary to hold the drop in suspension so it is completely surrounded by the fluid of the bath 14 rather than resting on a bottom wall of the container. Holding the drop in suspension is also required because the oscillation sensing apparatus 22 can monitor oscillations of the drop only when the drop lies within a limited area of the tank beside which the sensing apparatus has been positioned. In order to prevent a drop 16 of a fluid having a slightly different density than the fluid of the bath 14, from floating up to the top or sinking to the bottom of the bath, an acoustic standing wave pattern is established in the bath. This is accomplished by energizing the transducer 18 to apply acoustic waves of a second frequency which is resonant to the depth of the bath. In a typical application, the frequency utilized to generate resonant oscillations of the drop 16 may be on the order of a few cycles per second, or hertz, while the frequency utilized to establish a standing wave pattern in the bath may be on the order of kilohertz. The drop 16 will be urged toward a node (maximum pressure) or antinode (minimum pressure) of the standing wave pattern, depending upon whether the fluid of the drop has a higher or lower compressibility than the fluid of the bath. The levitation standing wave pattern also can be obtained by filling the container to the top, with extra fluid in an overflow tube 23, so sound is reflected off a reflecting wall 25 at the top of the bath, to prevent possible deformation of a free liquid top.

The oscillation sensing apparatus 22 includes a lamp 30 (FIG. 2) whose light rays are collimated by a lens 32.

The collimated rays pass through transparent walls of the container 12 and through the portion of the bath 14 which contains the drop 16. While the bath 14 contains transparent fluid, the drop 16 has been dyed so it is largely opaque, to thereby interrupt the middle portion of the collimated light beam. The light passing out of the tank, is intercepted by a slit device 34, which passes only a narrow slit of light. The narrow slit of light is concentrated by a lens 36 onto a photocell 38 which generates an electrical signal on line 40 proportional to the amount of light incident on the cell.

Figure 3:
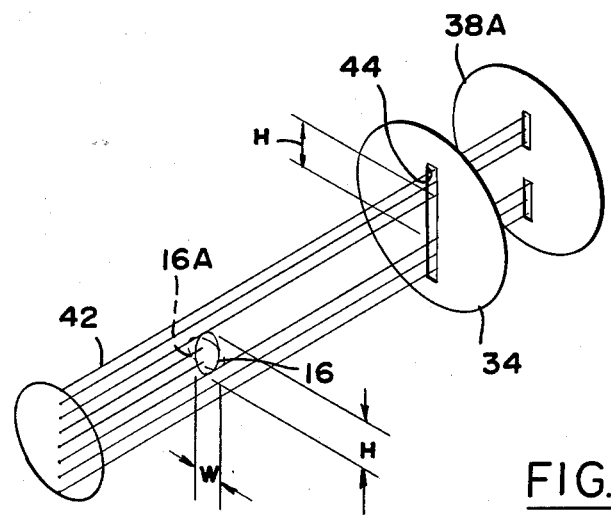
FIG. 3 is a partial simplified perspective view of the apparatus of FIG. 2, showing the principal of operation of the oscillation sensing apparatus.
Figure 2:
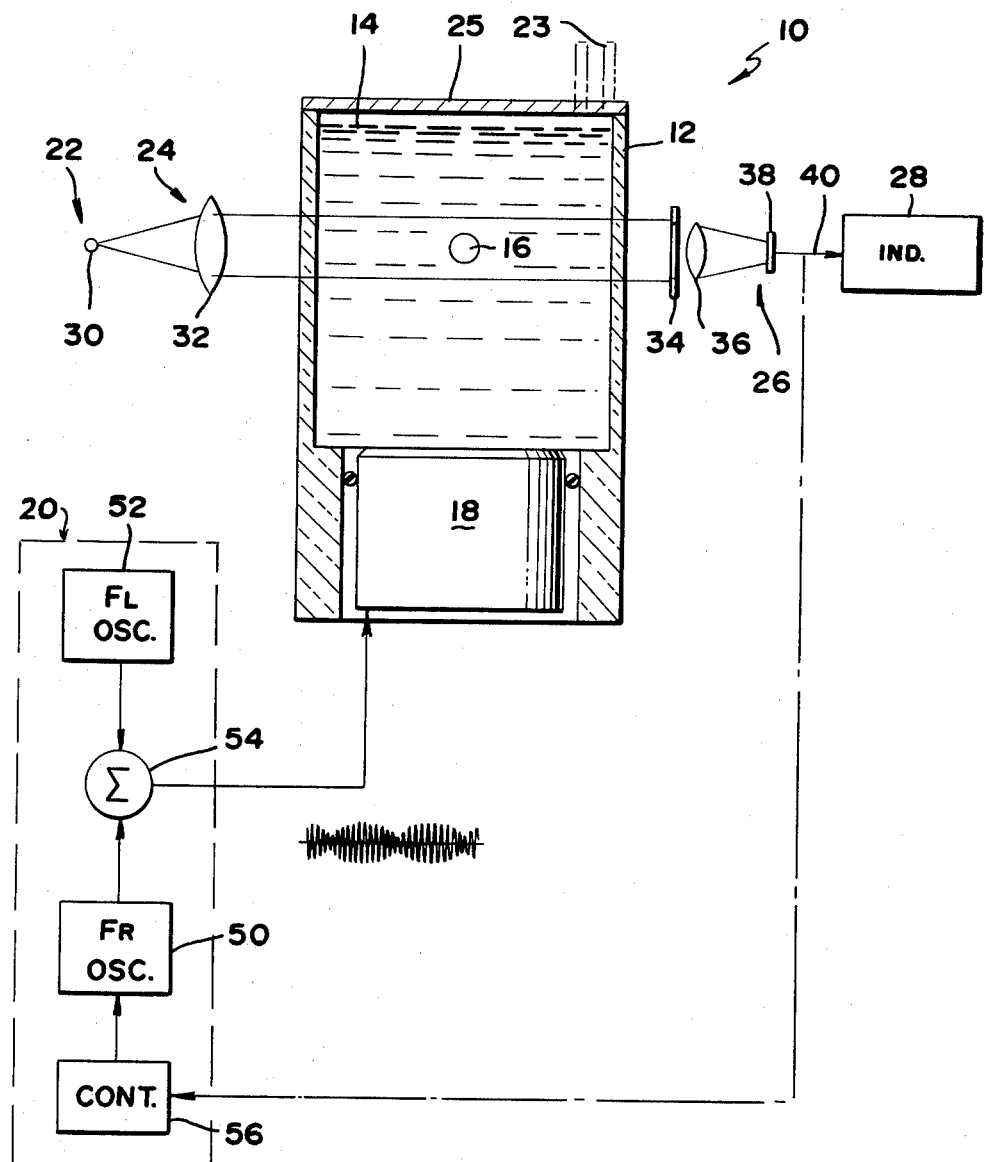
FIG. 2 is a sectional and block diagram view of the apparatus of FIG. 1.

FIG. 3 shows how a bundle of collimated rays 42 that are interrupted by the opaque drop 16, can be utilized to detect oscillations of the drop. In the absence of the drop 16, the entire length of the slit 44 of the slit device is illuminated. The presence of the drop 16 of a height H results in a middle section of the slit 44, of the same height H as the drop, being unilluminated. During oscillation of the drop, when it changes from the prolate position at 16 to the oblate position at 16A, the height H of the drop oscillates, to thereby vary the height H of the unilluminated portion of the slit. A photocell 38 A behind the slit, therefore receives a varying amount of light as the drop oscillates. In practice, the lens 36 and small photocell 38 of FIG. 2, are utilized to enable a smaller photocell to be employed. As the frequency of acoustic waves approaches a resonant oscillation frequency of the drop, the output of the photocell 38 begins to vary considerably. The amplitude of the AC portion of the photocell output on line 40, reaches a maximum at the precise resonant frequency of the drop. It is also possible to monitor oscillation of a transparent drop having a different index of refraction than that of the bath liquid by detecting light diffracted by the drop.

The oscillator apparatus 20 utilized to drive the transducer 18, is shown constructed with a resonance oscillator 50 which can produce the frequency of perhaps several Hz at which the drop resonates, a levitation oscillator 52 which produces a frequency such as several kHz (kilohertz) which produces a standing wave pattern within the bath 14 to hold the drop in position, and a mixer 54 which combines the two frequencies and delivers it to the transducer 18. It may be noted that instead of utilizing a resonant oscillator 50 of low frequency, a higher frequency oscillator can be utilized with its amplitude modulated at the low resonance frequency of the drop, to more efficiently drive the transducer. The higher frequency amplitude-modulated wave, is preferably of a frequency resonant to the depth of the bath. The photocell 38 of the oscillation sensor apparatus, can be utilized with its output 40 connected to a control 56 of the oscillator apparatus which controls the frequency of the resonant oscillator 50, as by varying the voltage to a voltage controlled oscillator. The control 56 can be utilized to sweep the frequency, at a slow rate such as 10 milihertz per second, until a maximum AC output from the photocell 38 is detected, and to indicate the frequency which gave rise to the maximum photocell output.

Knowledge as to the interfacial surface tension between the fluid of the drop 16 and the fluid of the bath 14, can be useful in a variety of analyzing techniques. In the monitoring of slow chemical reactions, which occur over a period of more than a few seconds, the monitoring of the surface tension can indicate the progress of the chemical reaction. This is because all chemical reactions change the molecular bond structure of the material, which changes the surface tension. The reaction can be one which occurs between the material of the drop 16 and the material of the surounding bath 14, in which case the resonant frequency can be monitored during a period immediately following the introduction of the drop into the bath. The reaction can also be one which occurs between components in the drop. The host or bath liquid should be substantially immiscible in the drop liquid to avoid immediate dispersion of the drop. A stable introduction of the drop can be performed by discharging a drop of precisely controlled size in a stable location of the acoustic standing wave structure, and immediately withdrawing the tube from which the drop was dispensed. In another application, additives can be placed in a drop, and a resonant oscillation frequency can be monitored to observe the rate of reaction of the additive with the rest of the material of the drop. For example, detergents or surfactants added to a drop of a liquid, will greatly affect the surface tension of the drop.

The resonant oscillation frequencies of a drop depend upon the size of the drop, the density of the fluid forming the drop, the density of the fluid forming the bath, and the molecular bond structure of the materials of the drop and of the bath. The size of the drop can be very closely controlled by easily available dispensing syringes, and the densities of the material of the drop and of the material of the bath can be accurately determined. Experiments that have been conducted indicate that the resonant frequency of a drop can be determined within 0.1%. Accordingly, when monitoring the changes in resonant frequency, the apparatus can be utilized to closely monitor the changes in the molecular bond structure of the fluids, and particularly of the drop when it lies in a large bath of substantially inert fluid.

The resonant frequencies of a drop of fluid in a surrounding bath of fluid, is given by the formula:

$$f_n = f_n' - \frac{a}{2\sqrt{f_n'}} + \frac{a^2}{4} \qquad \text{eq. 1}$$

wherein $f_n$ is the frequency of the $n^{th}$ mode of oscillation (with $n=2$ corresponding to the fundamental or lowest frequency oscillation mode), $f_n'$ is the Lamb's natural frequency of the drop, and $a$ is a parameter dependent upon the properties of the two fluids and particularly of the molecular bond structures of the two fluids. Lamb's natural frequency is given by the equation:

$$f_n'^2 = \frac{n(n-1)(n+1)(n+2)}{R^3[nd_0 + (n+1)d_i]} \sigma \qquad \text{eq. 2}$$

where $\sigma$ is the interfacial tension, R is the radius of the drop, and $d_o$ and $d_i$ are the densities of the outer liquid (i.e. bath) and inner liquid (i.e. drop) respectively.

$a$ is given by the equation:

$$a = \frac{(2n+1)\sqrt[2]{u_i u_o d_i d_o}}{\sqrt{2} \, R [nd_o + (n+1)d_i] \cdot [\sqrt{u_i d_i} + \sqrt{u_o d_o}]} \qquad \text{eq. 3}$$

where $u_o$ is the dynamic viscosity of the outer fluid (bath), $u_i$ is the dynamic viscosity of the inner fluid (drop), and $d_i$, $d_o$, and R are as defined above.

In one experiment that has been performed, a drop of silicone and carbon tetrachloride ($CCL_4$), containing a dye making it largely opaque, was introduced into a bath of water. The CCL₄ was added to the silicone to more closely match the density of the drop to that of the surrounding water. The fluid of the drop had a density of 0.995 grams per cm³, and a viscosity of 3.2 centistokes. The water bath 14 had a depth of about 6 inches (about 15 cm). The drop of silicone (with CCL₄ therein) had a volume of 1.9 cm³. It was found that the drop had a lowest resonant frequency of 3.56 Hz. From this, it was calculated that the interfacial tension of the drop to the bath was 37 dynes/cm. An acoustic standing wave pattern was established in the bath 14 by applying a frequency of 22 kHz to the transducer 18 at the bottom of the bath, which produces three equally spaced nodes (pressure maxima) along the height of the bath. The lowest resonant frequency along the depth of the bath is 5.5 kHz, which produces an antinode at the center but no nodes (except at the top and bottom), while an 11 kHz frequency produces one node located at the center of the height of the bath. However, a higher frequency was utilized because the particular transducer was more efficient at a higher frequency. Where the drop has a greater compressibility than that of the host medium of the surrounding bath, it gravitates towards the nearest node. The pressure of the standing wave pattern is highest along the vertical centerline of the bath, and decreases progressively further towards the edges of the bath, so that the drop tends to stay in the center. It is possible to retain a drop of lower compressibility than the surrounding bath, by utilizing additional transducers to set up a standing wave pattern in three dimensions.

The system of the present invention for determining resonant frequencies of oscillation of drops, can be utilized to measure a particular property of the material, as well as to monitor slow changes in the proper of the material. The determination of the amount of a contaminant or additive in a liquid can be more precisely obtained by the use of other instruments such as a mass spectrometer or by infrared or ultraviolet spectroscopy. However, the technique of the present invention enables a relatively coarse determination of the composition to be made rapidly and with relatively inexpensive equipment. The system of the present invention is very useful in monitoring slow physical reactions which occur over a period of a few seconds or more, and which are otherwise difficult to monitor, as in monitoring the diffusion of an additive in a fluid, or slow chemical reactions, by measuring changes in the resonant frequency of a drop. The resonant oscillations can also be utilized to mix a drop of material, as in distributing nutrients uniformly to a mass of cells forming the drop, to more effectively feed the cells. The term "drop" does not necessarily imply that the quantity of fluid is small, but only that it tends to remain as a mass which is a different material than that of the surrounding bath, at least for a short period.

Although physical properties of the drop material can be calculated, it is often useful to merely note the resonant frequency or changes in the resonant frequency of the drop. For example, the rate at which a chemical reaction is occurring, can be monitored by noting the rate at which the frequency changes, and the end of the reaction is indicated by the end of the frequency change. Decreases in the resonant frequency indicate decreases in the interfacial surface tension. It is generally desirable to utilize a host liquid of about the same density as the drop liquid, to minimize the required amplitude of the levitation acoustic energy. The levitation acoustic radiation itself produces a deformation in the drop from a spherical form, but this has an insignificant effect on the resonant frequencies of the drop for small levitation-induced deformations (of less than about 1%) and especially where the resonant oscillations are of small amplitude (where the change in drop diameter during oscillation is less than about 10%) normally utilized herein.

Thus, the present invention provides a method and apparatus which can be utilized to oscillate and measure the resonant frequency of oscillation of a drop of material, which can be utilized in determining the interfacial tension of a drop of material in a bath. This can be accomplished by introducing a drop of a first liquid in a bath of a second liquid, and applying acoustic waves to the bath, of a frequency close to a resonant oscillation frequency of the drop. The frequency is swept while the oscillation amplitude of the drop is monitored, to precisely determine a resonant oscillation frequency of the drop. Oscillations of the drop can be determined by projecting a light beam through a bath portion containing the drop and monitoring the variation of light received in a slit-area that would be fully illuminated in the absence of the drop, and with the slit-like area being blocked by only a strip-like portion passing through the center of the drop. The drop can be hled in approximate location to facilitate monitoring of its oscillations, by applying an acoustic standing wave pattern to the bath that contains the drop. The bath fluid is generally a liquid when the system is utilized on the earth, but may be a gas when utilized in a zero gravity environment.

Although particular embodiments of the invention have been described and illustrated herein, it is recognized that modifications and variations may readily occur to those skilled in the art and consequently, it is intended that the claims be interpreted to cover such modifications and equivalents.

What is claims is:

1. Apparatus useful in oscillating a drop of a first fluid when surrounded by a bath fluid, comprising:
   a container for holding a bath fluid and for receiving a drop of the first fluid within the bath fluid;
   transducer means coupled to said container and energizable for generating acoustic energy and conducting it into bath fluid lying in said container;
   means for energizing said transducer means; and
   means for sensing oscillations of the drop of first fluid;
   said energizing means being frequency controllable to alter the frequency to a value which produces resonant oscillations of said drop of first fluid.

2. The apparatus described in claim 1 wherein:
   said oscillation sensing means senses oscillations of a drop at a predetermined location within said container; and
   said energizing means energizes said transducer means to produce a levitation frequency that establish a standing wave pattern within said chamber that can hold said drop at said predetermined location, as well as to produce said resonant frequency value.

3. The apparatus described in claim 2 wherein:
   said levitation frequency is more than 100 Hz and said resonant frequency value varies within a range that includes a frequency less than one-tenth said levitation frequency.

4. The apparatus described in claim 1 wherein:
   said sensing means includes a source for directing a light beam past said drop, and a detector means positioned to intercept said light beam after it has passed said drop, for sensing changes in the width of the drop along a predetermined axis which is perpendicular to the direction of travel of said light beam past said drop.

5. Apparatus for oscillating a drop of a first liquid without contacting a solid, comprising:

a container;

a second liquid lying in said container and forming a liquid bath large enough to completely envelope said drop, said second liquid being substantially immiscible and chemically unreactive with said first liquid of said drop;

acoustic transducer means coupled to said second liquid; and means for energizing said transducer means to produce acoustic waves in said second liquid of a frequency which is resonant to said drop lying in said second liquid.

6. The apparatus described in claim 5 wherein:

said energizing means also energizes said transducer means at a second frequency which is chosen to establish a standing wave pattern of acoustic waves in said second liquid.

7. The apparatus described in claim 5 wherein:

said second liquid has substantially the same density as said first liquid of said drop.

8. Apparatus for oscillating and sensing oscillations of a substantially opaque suspended drop, comprising:

light source means for directing a beam of light of a diameter greater than the diameter of said drop when it is quiescent, at said drop;

means positioned on a side of said drop opposite said light source means, for detecting the amount of light falling on a slit-like area of predetermined size whose center portion is blocked from receiving light of said beam by said drop; and means for oscillating said drop so its diameter, as measured parallel to the length of said slit-like area, repeatedly changes.

9. The apparatus described in claim 8 wherein:

said detecting means includes a slit device having a slit and a photosensitive cell located behind said slit for detecting light passing through said slit.

10. A method for sensing interfacial surface tension at a surface of a first liquid comprising:

introducing a drop of the first liquid in a bath of a second liquid;

applying acoustic energy to said bath of second liquid;

sensing oscillations of said drop; and varying the frequency of said applied acoustic energy to a frequency at which said drop undergoes resonant oscillations.

11. The method described in claim 10 including:

applying second acoustic energy to said bath of a wavelength which produces a standing wave pattern in said bath while also applying said first mentioned acoustic energy, whereby to urge said drop toward a predetermined location in said bath.

12. The method described in claim 10 wherein:

said step of sensing oscillations includes directing a collimated light beam of larger width than said drop through said bath, and detecting light falling on a slit area of smaller width but larger length than the diameter of the light beam area blocked by said drop when it is quiescent.

13. The method described in claim 10 wherein:

said second liquid has about the same density as said first liquid.

14. The method described in claim 10 wherein:

said second liquid is substantially transparent, said step of sensing oscillations includes directing a light beam through said bath; and including adding a dye to said first liquid to make it substantially opaque.

* * * * *